United States Patent
Hanley et al.

(10) Patent No.: US 10,125,082 B2
(45) Date of Patent: Nov. 13, 2018

(54) METHOD FOR COUPLING A FIRST COMPOUND TO A SECOND COMPOUND

(71) Applicant: Dow Global Technologies LLC, Midland, MI (US)

(72) Inventors: Patrick S. Hanley, Midland, MI (US); Jossian Oppenheimer, Midland, MI (US); Matthias S. Ober, Midland, MI (US); William J. Kruper, Jr., Sanford, MI (US); Arkady L. Krasovskiy, Freeport, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 15/515,069

(22) PCT Filed: Oct. 8, 2015

(86) PCT No.: PCT/US2015/054654
§ 371 (c)(1),
(2) Date: Mar. 28, 2017

(87) PCT Pub. No.: WO2016/057771
PCT Pub. Date: Apr. 14, 2016

(65) Prior Publication Data
US 2017/0240499 A1 Aug. 24, 2017

Related U.S. Application Data

(60) Provisional application No. 62/149,233, filed on Apr. 17, 2015, provisional application No. 62/061,638, filed on Oct. 8, 2014.

(51) Int. Cl.
| | |
|---|---|
| *C07C 67/343* | (2006.01) |
| *C07C 41/30* | (2006.01) |
| *C07C 231/12* | (2006.01) |
| *C07D 213/55* | (2006.01) |
| *C07C 2/86* | (2006.01) |
| *C07D 317/60* | (2006.01) |
| *C07C 67/31* | (2006.01) |

(52) U.S. Cl.
CPC ............ *C07C 67/343* (2013.01); *C07C 2/868* (2013.01); *C07C 41/30* (2013.01); *C07C 67/31* (2013.01); *C07C 231/12* (2013.01); *C07D 213/55* (2013.01); *C07D 317/60* (2013.01); *C07C 2531/20* (2013.01); *C07C 2531/22* (2013.01); *C07C 2531/24* (2013.01)

(58) Field of Classification Search
CPC ..... C07C 67/343; C07C 231/12; C07C 41/30; C07C 67/31; C07C 2/868; C07C 2531/24; C07C 2531/22; C07C 2531/20; C07D 213/55; C07D 317/60
See application file for complete search history.

(56) References Cited

PUBLICATIONS

Kantchev, E.A.B., "Palladium Complexes of N-Heterocyclic Carbenes as Catalysts for Cross-Coupling Reactions—A Synthetic Chemist's Perspective." Angewandte Chemie International Edition 46.16 (2007): 2768-2813. (Year: 2007).*
So, C. M., "Palladium-catalyzed cross-coupling reactions of aryl mesylates." Chemical Society Reviews 40.10 (2011): 4963-4972. (Year: 2011).*
Farina, V., "The Stille Reaction." Organic reactions (1997). (Year: 1997).*
Baker, S. R., "Palladium in Cephalosporin Chemistry: Mild Triflate Couplings in the Absence of Phosphines and Halide Donors." Synthetic Communications 20.14 (1990): 2185-2189.*
Irina P> Beletskaya et all: "The Heck Reaction as a Sharpening Stone of Palladium Catalysis" Chem. Rev. 2000, vol. 100, pp. 3009-3066.
Armin De Meijere et al: "Fine Feathers Make Fine Birds: The Heck Reaction in Modern Garb." Angew. Chem. Int. Ed. Engl. 1994, vol. 33, pp. 2379-2411.
Dennis McCartney et al: "The Asymmetric Heck and related reactions" Chem. Soc. Rev., 2011, vol. 40, pp. 5122-5150.
Kuppusamy Kanagaraj et al: "The Aminocyclodextrin/Pd(OAc)2 Complex as an Efficient Catalyst for the Mizoroki-Heck Cross-Coupling Reaction", Chemistry—A European Journal vol. 19, No. 43, Oct. 18, 2013 (Oct. 18, 2013), pp. 14425-14431.
Walter Cabri et al: "Ligand-control led .alpha.-regioselectivity in palladium-catalyzed arylation of butyl vinyl ether", The Journal of Organic Chemistry, vol. 55, No. 11, May 1990 (May 1990), pp. 3654-3655.
Walter Cabri et al: "1, 10-Phenanthroline derivatives: a new ligand class in the Heck reaction. Mechanistic aspects", The Journal of Organic Chemistry, vol. 58, No. 26, Dec. 1993 (Dec. 1993), pp. 7421-7426.
Al-Yun Peng et al: "Pd(0) /iodide salt-mediated Heck reaction of aryl nonaflates: Application to the synthesis of 2-(I-alkenyl) phenylphosphonates", Journal of Fluorine Chemistry, Elsevier, NL, vol. 132, No. 11, Jun. 22, 2011 (Jun. 22, 2011), pp. 982-986.
Jiajia Dong et al: "SuFEx-Based Synthesis of Polysulfates", Angewandte Chemie International Edition, vol. 53, No. 36, Aug. 5, 2014 (Aug. 5, 2014), pp. 9466-9470.
Chen Q-V et al: "Palladium-Catalyzed 1-12 Reaction of Phenyl Fluoroalkanesulfonates With Alkynes and Alkenes", Tetrahedron Letters, Pergamon, GB, vol. 27, No. 10, Jan. 1986 (Jan. 1986), pp. 1171-1174.
Sarah Z. Tasker et al: "Nickel-Catalyzed Mizoroki-Heck Reaction of Aryl Sulfonates and Chlorides with Electronically Unbiased Terminal Olefins: High Selectivity for Branched Products", Angewandte Chemie International Edition, vol. 53, No. 7, Feb. 10, 2014 (Feb. 10, 2014), pp. 1858-1861.

(Continued)

*Primary Examiner* — John M Mauro
(74) *Attorney, Agent, or Firm* — Jonathan D. Baskini

(57) ABSTRACT

The present disclosure describes a method of coupling a first compound to a second compound, the method comprising: providing the first compound having a fluorosulfonate substituent; providing the second compound comprising an alkene; and reacting the first compound and the second compound in a reaction mixture, the reaction mixture including a catalyst having at least one group 10 atom, the reaction mixture under conditions effective to couple the first compound to the second compound.

20 Claims, No Drawings

(56) References Cited

PUBLICATIONS

Gregory P Roth et al: "Palladium cross-coupling reactions of aryl fluorosulfonates: An alternative to triflate chemistry", The Journal of Organic Chemistry, American Chemical Society, US, vol. 56, No. 11, Jan. 1991 (Jan. 1991), pp. 3493-3496.

Gregory P. Roth et al: "Alkoxycarbonylation Reactions Using Aryl Fluorosulfonates", Tetrahedron Letters, vol. 33, No. 15, Apr. 1992 (Apr. 1992), pp. 1959-1962.

Michael A. McGuire et al: "A Novel, Practical Synthesis of Estra-I,3,5(10)-triene-3,17.beta.-dicarboxylic Acid 17-tert-Butylamide (SK&F 105656) from Estrone, via a Palladium-Catalyzed Methoxycarbonylation of a 3-Fluorosulfonate", The Journal of Organic Chemistry, vol. 59, No. 22, Nov. 1994 (Nov. 1994), pp. 6683-6686.

\* cited by examiner

METHOD FOR COUPLING A FIRST COMPOUND TO A SECOND COMPOUND

BACKGROUND

Heck (or Mizoroki-Heck) coupling is a valuable synthetic method for coupling compounds, thereby forming a new carbon-carbon bond between a first compound and a second compound. Traditionally, Heck coupling partners consist of a first compound having a halide or triflate (trifluoromethanesulfonate) substituent and a second compound comprising an alkene.

It is known that triflates, having the formula $F_3CSO_2-$, may be used in the place of the halides in Heck couplings, however the expense of triflic anhydride $(CF_3SO_2)_2O$ has limited the use of triflates in Heck couplings to the production of fine chemicals. Further, the atom economy of triflic anhydride is low since half of the molecule is expended as monomeric triflate anion $(CF_3SO_2^-)$ as a result of condensation with a phenolic precursor.

In addition, it is recognized that some compounds having a triflate substituent hydrolyze in the presence of water, and therefore can require anhydrous conditions to achieve high yield and selectivity. In such cases it is further recognized that unless anhydrous conditions are employed, the amount of ligand and catalyst relative to substrate must be high to achieve reasonable yields.

It is also known that aryl methanesulfonates (also known as mesylates) are suitable for Heck couplings, for example aryl-olefin couplings. One drawback of coupling reactions using aryl methanesulfonates is that these reactions require expensive palladium catalysts. When performing a Heck coupling using either a triflate or methanesulfonate, it is common to perform the reaction in two steps, a first step comprising replacing the hydroxyl group on a first compound with the triflate or the methanesulfonate, and a second step comprising coupling the first compound with the second compound. A separation step is generally required between the first and second steps.

It would be desirable to have a replacement for triflates and methanesulfonates which allow Heck coupling reactions. Furthermore, a water-stable triflate replacement could ensure lower loadings of expensive catalysts. In addition, it is desired to have a cross-coupling reaction which has greater atom economy.

STATEMENT OF INVENTION

In one aspect, the present disclosure describes a method of coupling a first compound to a second compound, the method comprising: providing the first compound having a fluorosulfonate substituent; providing the second compound comprising an alkene; and reacting the first compound and the second compound in a reaction mixture, the reaction mixture including a catalyst having at least one group 10 atom, the reaction mixture under conditions effective to couple the first compound to the second compound.

In one aspect, a method is provided for coupling a first compound $A^1$ to a second compound $A^2$, as illustrated in Equation 1, comprising:

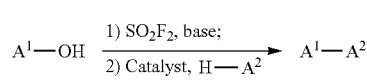

Equation 1 providing sulfuryl fluoride, a base and the first compound $A^1$ having a hydroxyl substituent to a reaction mixture, the first compound comprising an aryl or a heteroaryl group; providing a catalyst having at least one group 10 atom and the second compound $A^2$ to the reaction mixture, the second compound $A^2$ comprising an alkene of the form shown in Equation 4,

Equation 4 wherein the second compound includes three R substituents, wherein each R substituent is independently Hydrogen, an aryl group, a heteroaryl group, an alkyl group, a cycloalkyl group, a nitro group, a halide, a nitrogen, a cyano group, a carboxyester group, an acetoxy group, a substituted alkyl, aryl, heteroaryl or cycloalkyl group, or any two of the R groups are constituent parts of a ring system; and allowing the reaction mixture to react under conditions to produce the product shown in Equation 1.

DETAILED DESCRIPTION

Unless otherwise indicated, numeric ranges, for instance "from 2 to 10," are inclusive of the numbers defining the range (e.g., 2 and 10).

Unless otherwise indicated, ratios, percentages, parts, and the like are by moles.

As used herein, unless otherwise indicated, the phrase "molecular weight" refers to the number average molecular weight as measured in the conventional manner.

"Alkene," as used in this specification, refers to an unsaturated hydrocarbon, having at least one carbon-carbon double bond. In one instance, the alkene is substituted, for example, with alkyl, aryl, heteroaryl, heteroalkyl, carbonyl, or other suitable substituents. Examples of alkenes include, but are not limited to, acrylates, methacrylates, acrylonitrile, styrene, acrylamide, and allenes.

"Alkyl," as used in this specification, whether alone or as part of another group (e.g., in dialkylamino), encompasses straight and branched chain aliphatic groups having the indicated number of carbon atoms. If no number is indicated (e.g., aryl-alkyl-), then 1-12 alkyl carbons are contemplated. Preferred alkyl groups include, without limitation, methyl, ethyl, propyl, isopropyl, butyl, isobutyl, sec-butyl, tert-butyl, pentyl, hexyl and tert-octyl.

The term "heteroalkyl" refers to an alkyl group as defined above with one or more heteroatoms (nitrogen, oxygen, sulfur, phosphorus) replacing one or more carbon atoms within the radical, for example, an ether or a thioether.

An "aryl" group refers to any functional group or substituent derived from an aromatic ring. In one instance, aryl refers to an aromatic moiety comprising one or more aromatic rings. In one instance, the aryl group is a $C_6$-$C_{18}$ aryl group. In one instance, the aryl group is a $C_6$-$C_{10}$ aryl group. In one instance, the aryl group is a $C_{10}$-$C_{18}$ aryl group. Aryl groups contain 4n+2 pi electrons, where n is an integer. The aryl ring may be fused or otherwise attached to one or more heteroaryl rings, aromatic or non-aromatic hydrocarbon rings or heterocycloalkyl rings. Preferred aryls include, without limitation, phenyl, naphthyl, anthracenyl, and fluorenyl. Unless otherwise indicated, the aryl group is optionally substituted with 1 or more substituents that are compatible with the syntheses described herein. Such substituents include, but are not limited to, sulfonate groups, boron-containing groups, alkyl groups, nitro groups, halogens, cyano groups, carboxylic acids, esters, amides, $C_2$-$C_8$ alkene, and other aromatic groups. Other substituents are known in the art. Unless otherwise indicated, the foregoing substituent groups are not themselves further substituted.

"Heteroaryl" refers to any functional group or substituent derived from an aromatic ring and containing at least one heteroatom selected from nitrogen, oxygen, and sulfur. Preferably, the heteroaryl group is a five or six-membered ring. The heteroaryl ring may be fused or otherwise attached to one or more heteroaryl rings, aromatic or non-aromatic hydrocarbon rings or heterocycloalkyl rings. Examples of heteroaryl groups include, without limitation, pyridine, pyrimidine, pyridazine, pyrrole, triazine, imidazole, triazole, furan, thiophene, oxazole, thiazole. The heteroaryl group may be optionally substituted with one or more substituents that are compatible with the syntheses described herein. Such substituents include, but are not limited to, fluorosulfonate groups, boron-containing groups, $C_1$-$C_8$ alkyl groups, nitro groups, halogens, cyano groups, carboxylic acids, esters, amides, $C_2$-$C_8$ alkene and other aromatic groups. Other substituents are known in the art. Unless otherwise indicated, the foregoing substituent groups are not themselves further substituted.

"Aromatic compound" refers to a ring system having 4n+2 pi electrons where n is an integer.

As noted above, the present disclosure describes a process for coupling a first compound to a second compound. This process is shown generally in Equation 1, whereby a first compound having a hydroxyl group is first reacted with $SO_2F_2$ and a base and is second reacted with a second compound comprising an alkene in the presence of a catalyst. It is understood that where a hydroxyl group is indicated, the hydroxyl group could be deprotonated to form a phenolate (e.g. the deprotonation step could be performed prior to introduction of $A^1$ to the reaction mixture or after the introduction to the reaction mixture).

Equation 1

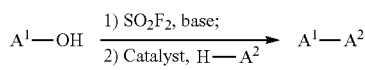

Unexpectedly, it has been found that the reaction of Equation 1 may be performed as a one-pot reaction, as compared to performing the reaction in discrete steps. Without being limited by theory, it is anticipated that the reaction shown in Equation 1 proceeds along the same reaction path whether performed as a one-pot reaction or as discrete steps. When performed in discrete steps, the first step comprises reacting a first compound having a hydroxyl substituent with $SO_2F_2$ to yield the product shown in Equation 2, and the second step comprises reacting the product of Equation 2 with a second compound comprising an alkene to yield the product shown in Equation 3.

Equation 2

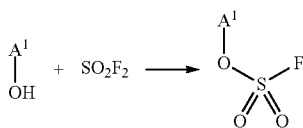

Equation 3

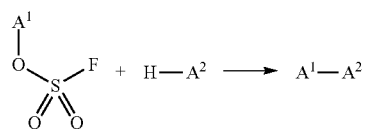

In one instance, the process involves a one-pot reaction where a first compound having a hydroxyl group is first reacted with $SO_2F_2$ and a base and is second reacted with a second compound comprising an alkene in the presence of a catalyst, as shown generally in Equation 1. Without being limited by theory, it is expected that Equation 3 is the same general reaction as depicted by step 2) of the reaction shown in Equation 1.

As used in Equation 1, Equation 2 and Equation 3, the first compound is identified as $A^1$ and the second compound is identified as $A^2$. In one instance, the first compound is either an aryl group or a heteroaryl group, or other substituent as is known to be coupled in the Heck coupling. In one instance, the second compound $A^2$ is an alkene of the form shown in Equation 4.

Equation 4

In one instance, the second compound $A^2$ is an alkene having three R substituents and is joined to a Hydrogen. As shown, it is contemplated that any of the three R substituents may be positioned at any of the two carbons forming the double bond of the alkene and the Hydrogen is positioned at the remaining position. The result of the reactions shown is the formation of a new carbon-carbon bond between the first compound and the second compound, thereby coupling the first compound to the second compound at the double bond of the alkene. In one instance, the new carbon-carbon bond is formed between the carbon of $A^1$ which is joined to the Oxygen and the carbon of $A^2$ which is joined to the Hydrogen, as illustrated in Equation 3. In one instance, the selection of reaction conditions, for example the selected catalyst, base, solvent and/or reactant substrate, can be used to increase the selectivity of a given product.

As noted above in the first step of Equation 3 and in Equation 2, the first compound, $A^1$, is bonded to a fluorosulfonate group. A fluorosulfonate group refers to O-fluorosulfonate of the formula —$OSO_2F$. O-fluorosulfonate may be synthesized from sulfuryl fluoride. The fluorosulfonate group serves as a leaving group from the first aromatic compound. Without being limited by theory, the sulfuryl atom of the fluorosulfonate group is bonded to the oxygen of the hydroxyl group of the first aromatic compound.

As noted above, the second compound, $A^2$, is an alkene including Hydrogen, an aryl group, a heteroaryl group, an alkyl group, a cycloalkyl group, a nitro group, a halide, a nitrogen, a cyano group, a carboxyester group, an acetoxy group, a substituted alkyl, aryl, heteroaryl or cycloalkyl group, or other substituent suitable for use in a Heck coupling. In one instance, any two of the R groups are constituent parts of a ring system. For example, R may be $C_{1-18}$ alkyl, $C_{3-18}$ cycloalkyl, $C_{6-18}$ aryl, or H.

As noted above in Equation 1 and Equation 3, the first compound is reacted with the second compound in a reaction mixture. The reaction mixture includes a catalyst having at least one group 10 atom. In some instances, the reaction mixture includes a ligand. In some instances, the reaction mixture includes a base. The group 10 atoms include nickel, palladium and platinum.

The catalyst is provided in a form suitable to the reaction conditions. In one instance, the catalyst is provided on a substrate. In one instance, the catalyst having at least one group 10 atom is generated in situ from one or more precatalysts and one or more ligands. Examples of palladium precatalysts include, but are not limited to, Palladium (II) acetate, Palladium(II) chloride, Dichlorobis(acetonitrile)

palladium(II), Dichlorobis(benzonitrile)palladium(II), Allylpalladium chloride dimer, Palladium(II) acetylacetonate, Palladium(II) bromideBis(dibenzylideneacetone)palladium(0), Bis(2-methylallyl)palladium chloride dimer, Crotylpalladium chloride dimer, Dichloro(1,5-cyclooctadiene) palladium(II), Dichloro(norbornadiene)palladium(II), Palladium(II) trifluoroacetate, Palladium(II) benzoate, Palladium(II) trimethylacetate, Palladium(II) oxide, Palladium (II) cyanide, Tris(dibenzylideneacetone)dipalladium(0), Palladium(II) hexafluoroacetylacetonate, cis-Dichloro(N,N,N', N'-tetramethylethylenediamine) palladium(II), and Cyclopentadienyl[(1,2,3-n)-1-phenyl-2-propenyl]palladium (II).

In one instance, nickel-based catalysts are used. In another instance, platinum-based catalysts are used. In yet another instance, a catalyst including one or more of nickel, platinum and palladium-based catalysts are used.

In one instance, pyridine-enhanced precatalyst preparation stabilization and initiation (PEPPSI) type catalysts are used, for example, [1,3-Bis(2,6-Diisopropylphenyl)imidazol-2-ylidene](3-chloropyridyl)palladium(II) dichloride, and (1,3-Bis(2,6-diisopropylphenyl)imidazolidene) (3-chloropyridyl) palladium(II) dichloride.

Examples of nickel precatalysts include, but are not limited to, nickel(II) acetate, nickel(II) chloride, Bis(triphenylphosphine)nickel(II) dichloride, Bis(tricyclohexylphosphine)nickel(II) dichloride, [1,1'-Bis(diphenylphosphino) ferrocene]dichloronickel(II), Dichloro[1,2-bis (diethylphosphino)ethane]nickel(II), Chloro(1-naphthyl)bis (triphenylphosphine)nickel(II), 1,3-Bis(2,6-diisopropylphenyl)imidazolium chloride, Bis(1,5-cyclooctadiene)nickel(0), Nickel(II) chloride ethylene glycol dimethyl ether complex, [1,3-Bis(diphenylphosphino)propane]dichloronickel(II), [1,2-Bis(diphenylphosphino)ethane]dichloronickel(II), and Bis(tricyclohexylphosphine)nickel(0).

The ligand used in the reaction mixture is preferably selected to generate the selected catalyst from a pre-catalyst. For example, the ligand may be a phosphine ligand, a carbene ligand, an amine-based ligand, a carboxylate based ligand, an aminodextran, an aminophosphine-based ligands or an N-heterocyclic carbene-based ligand. In one instance, the ligand is monodentate. In one instance, the ligand is bidentate. In one instance, the ligand is polydentate.

Suitable phosphine ligands may include, but are not limited to, mono- and bi-dentate phosphines containing functionalized aryl or alkyl substituents or their salts. For example, suitable phosphine ligands include, but are not limited to, triphenylphosphine; Tri(o-tolyl)phosphine; Tris (4-methoxyphenyl)phosphine; Tris(pentafluorophenyl) phosphine; Tri(p-tolyl)phosphine; Tri(2-furyl)phosphine; Tris(4-chlorophenyl)phosphine; Di(1-adamantyl)(1-naphthoyl)phosphine; Benzyldiphenylphosphine; 1,1'-Bis(di-t-butylphosphino)ferrocene; (−)-1,2-Bis((2R,5R)-2,5-dimethylphospholano)benzene; (−)-2,3-Bis[(2R,5R)-2,5-dimethylphospholanyl]-1-[3,5-bis(trifluoromethyl)phenyl]-1H-pyrrole-2,5-dione; 1,2-Bis(diphenylphosphino)benzene; 2,2'-Bis(diphenylphosphino)-1,1'-binaphthyl; 2,2'-Bis(diphenylphosphino)-1,1'-biphenyl, 1,4-Bis(diphenylphosphino)butane; 1,2-Bis(diphenylphosphino)ethane; 2-[Bis (diphenylphosphino)methyl]pyridine; 1,5-Bis (diphenylphosphino)pentane; 1,3-Bis(diphenylphosphino) propane; 1,1'-Bis(di-i-propylphosphino)ferrocene; (S)-(−)-5,5'-Bis[di(3,5-xylyl)phosphino]-4,4'-bi-1,3-benzodioxole; tricyclohexylphosphine (referred to herein as PCy3); Tricyclohexylphosphine tetrafluoroborate (referred to herein as PCy3.HBF$_4$); N-[2-(di-1-adamantylphosphino) phenyl]morpholine; 2-(Di-t-butylphosphino)biphenyl; 2-(Di-t-butylphosphino)-3,6-dimethoxy-2',4',6'-tri-i-propyl-1,1'-biphenyl; 2-Di-t-butylphosphino-2'-(N,N-dimethylamino) biphenyl; 2-Di-t-butylphosphino-2'-methylbiphenyl; Dicyclohexylphenylphosphine; 2-(Dicyclohexylphosphino)-3,6-dimethoxy-2',4',6'-tri-i-propyl-1; 2-(Dicyclohexylphosphino)-2'-(N,N-dimethylamino)biphenyl; 2-Dicyclohexylphosphino-2',6'-dimethylamino-1,1'-biphenyl; 2-Dicyclohexylphosphino-2',6'-di-i-propoxy-1,1'-biphenyl; 2-Dicyclohexylphosphino-2'-methylbiphenyl; 2-[2-(Dicyclohexylphosphino)phenyl]-1-methyl-1H-indole; 2-(Dicyclohexylphosphino)-2',4',6'-tri-i-propyl-1,1'-biphenyl; [4-(N,N-Dimethylamino)phenyl]di-t-butylphosphine; 9,9-Dimethyl-4,5-bis(diphenylphosphino)xanthene; (R)-(−)-1-[(S)-2-(Diphenylphosphino)ferrocenyl] ethyldicyclohexylphosphine; Tribenzylphosphine; Tri-t-butylphosphine; Tri-n-butylphosphine; and 1,1'-Bis (diphenylphosphino)ferrocene.

Suitable amine and aminophosphine-based ligands include any combination of monodentate or bidentate alkyl and aromatic amines including, but not limited to, pyridine, 2,2'-Bipyridyl, 4,4'-Dimethyl-2,2'-dipyridyl, 1,10-Phenanthroline, 3,4,7,8-Tetramethyl-1,10-phenanthroline, 4,7-Dimethoxy-1,10-phenanthroline, N,N,N',N'-Tetramethylethylenediamine, 1,3-Diaminopropane, ammonia, 4-(Aminomethyl)pyridine, (1R,2S,9S)-(+)-11-Methyl-7,11-diazatricyclo[7.3.1.0$^{2,7}$]tridecane, 2,6-Di-tert-butylpyridine, 2,2'-Bis[(4S)-4-benzyl-2-oxazoline], 2,2-Bis((4S)-(−)-4-isopropyloxazoline)propane, 2,2'-Methylenebis[(4S)-4-phenyl-2-oxazoline], and 4,4'-di-tert-butyl-2,2'bipyridyl. In addition, aminophosphine ligands such as 2-(Diphenylphosphino)ethylamine, 2-(2-(Diphenylphosphino)ethyl)pyridine, (1R,2R)-2-(diphenylphosphino)cyclohexanamine, an aminodextran and 2-(Di-tert-butylphosphino)ethylamine.

Suitable carbene ligands include N-heterocyclic carbene (NHC) based ligands, including, but not limited to, 1,3-Bis (2,4,6-trimethylphenyl)imidazolinium chloride, 1,3-Bis(2,6-diisopropylphenyl)imidazolium chloride, 1,3-Bis-(2,6-diisopropylphenyl) imidazolinium chloride, 1,3-Diisopropylimidazolium chloride, and 1,3-Dicyclohexylbenzimidazolium chloride.

The base used in the reaction mixture is selected to be compatible with the catalyst, the alkene and the fluorosulfonate. Suitable bases include, but are not limited to, carbonate salts, phosphate salts, acetate salts and carboxylic acid salts. Inorganic bases are suitable in the reaction mixture. As used herein, "inorganic base" refers to non-organic bases, for example, carbonate salts, phosphate salts, and acetate salts.

Examples of carbonate salts include, but are not limited to, lithium carbonate, sodium carbonate, potassium carbonate, rubidium carbonate, cesium carbonate, ammonium carbonate, substituted ammonium carbonates, and the corresponding hydrogen carbonate salts. Examples of phosphate salts include, but are not limited to, lithium phosphate, sodium phosphate, potassium phosphate, rubidium phosphate, cesium phosphate, ammonium phosphate, substituted ammonium phosphates, and the corresponding hydrogen phosphate salts. Examples of acetate salts include, but are not limited to, lithium acetate, sodium acetate, potassium acetate, rubidium acetate, cesium acetate, ammonium acetate, and substituted ammonium acetates.

Other bases include, but are not limited to, salts of formate, fluoroacetate, and propionate anions with lithium, sodium, potassium, rubidium, cesium, ammonium, and substituted ammonium cations; metal hydroxides, such as lithium hydroxide, sodium hydroxide, potassium hydroxide, metal dihydroxides such as magnesium dihydroxide, calcium dihydroxide, strontium dihydroxide, and barium dihydroxide; metal trihydroxides such as aluminum trihydroxide, gallium trihydroxide, indium trihydroxide, thallium trihydroxide; non nucleophilic organic amines such as triethylamine, N,N-diisopropylethylamine, 1,4-diazabicyclo[2.2.2]octane (DABCO), 1,5-Diazabicyclo[4.3.0] non-5-ene (DBN), 1,8-Diazabicyclo[5.4.0]undec-7-ene (DBU); bis(silyl)amide salts such as the lithium, sodium, and potassium salts of bis(trimethylsilyl)amide; alkoxide salts such as the lithium, sodium, and potassium salts of t butoxide; and 1,8-bis(dimethylamino) naphthalene; metal hydrides, such as lithium hydride, sodium hydride and potassium hydride; metal fluorides, such as sodium fluoride, potassium fluoride, cesium fluoride, silver fluoride, tetra butyl ammonium fluoride, ammonium fluoride, triethyl ammonium fluoride.

Examples of amine bases, such as alkylamines and heteroarenes include, but are not limited to, triethylamine, pyridine, morpholine, 2,6-lutidine, triethylamine, N,N-Dicyclohexylmethylamine, and diisopropylamine. Other examples of amine bases include non nucleophilic organic amines such as triethylamine, N,N-diisopropylethylamine, 1,4-diazabicyclo[2.2.2]octane (DABCO), 1,5-Diazabicyclo[4.3.0]non-5-ene (DBN), 1,8-Diazabicyclo[5.4.0]undec-7-ene (DBU), bis(silyl)amide salts such as the lithium, sodium, and potassium salts of bis(trimethylsilyl)amide.

In one instance, the base is used in the presence of a phase-transfer catalyst. In another instance, the base is used in the presence of water. In yet another instance, the base is used in the presence of an organic solvent. In still another instance, the base is used in the presence of one or more of a phase-transfer catalyst, water or an organic solvent.

Preferably, at least one equivalent of base is present for each equivalent of fluorosulfonate. In some embodiments, no more than 10 equivalents of base are present for each equivalent of fluorosulfonate. In some embodiments, at least 2 equivalents of base are present for each equivalent of fluorosulfonate. In some embodiments, no more than 6 equivalents of base are present for each equivalent of fluorosulfonate.

The solvent in the reaction mixture is selected such that it is suitable for use with the reactants, the catalyst, the ligand and the base. For example, suitable solvents include, but are not limited to, toluene, xylenes (ortho-xylene, meta-xylene, para-xylene or mixtures thereof), benzene, water, methanol, ethanol, 1-propanol, 2-propanol, n-butanol, 2-butanol, pentanol, hexanol, tert-butyl alcohol, tert-amyl alcohol, ethylene glycol, 1,2-propanedioal, 1,3-propanediol, glycerol, N-methyl-2-pyrrolidone, acetonitrile, N,N-dimethylformamide, methyl acetate, ethyl acetate, propyl acetate, isopropyl acetate, triacetin, acetone, methyl ethyl ketone, and ethereal solvents, such as 1,4-dioxane, tetrahydrofuran, 2-methyltetrahydrofuran, diethylether, cyclopenyl methyl ether, 2-butyl ethyl ether, dimethoxyethane, polyethyleneglycol, dimethylacetamide (DMA), dimethylsulfoxide (DMSO), and 1,2-dichloroethane (DCE). In one instance, the solvent includes any combination of the solvents described herein, in, or in the absence of, a surfactant. In one instance, the sulfuryl fluoride is used neat at a sufficiently low temperature that the sulfuryl fluoride is in a liquid. In one instance, water is included in the reaction mixture.

One benefit of using fluorosulfonates as compared to triflates, is that the reaction can be carried out without a subsequent separation step, or with a simple separation step. In Heck couplings involving triflates, a dedicated purification step is required to remove byproducts since the products and the byproducts typically occupy the same phase. In the reaction schemes described herein, the byproducts are either in the gas phase, and will bubble out spontaneously or with a simple degassing step, or will partition into the aqueous phase, which is easily separable. As such, the reaction scheme described herein provides additional benefits as compared to Heck couplings involving triflates.

In one instance, the reaction described herein is completed as a one-pot reaction as shown in Equation 1. In a first step, a first compound having an alcohol substituent is added to a reaction mixture in the presence of sulfuryl fluoride and a base. The base may be any of the bases described herein, including, without limitation, amine bases and inorganic bases. This first step couples the fluorosulfonate substituent to the oxygen of the hydroxyl group. To the reaction mixture formed during this first step is added a second compound comprising an alkene and a catalyst. The catalyst may be a suitable group 10 catalyst, including, without limitation, platinum, palladium and nickel catalysts. The product of this second step is a compound formed by coupling the first aromatic compound and the second compound.

Some embodiments of the invention will now be described in detail in the following Examples. Unless stated otherwise, reported yields are ±5%.

Example 1

In this example p-tolyl sulfofluoridate is reacted with 2-ethylhexyl acrylate to yield 2-ethylhexyl (E)-3-(p-tolyl) acrylate as shown in Equation 2.

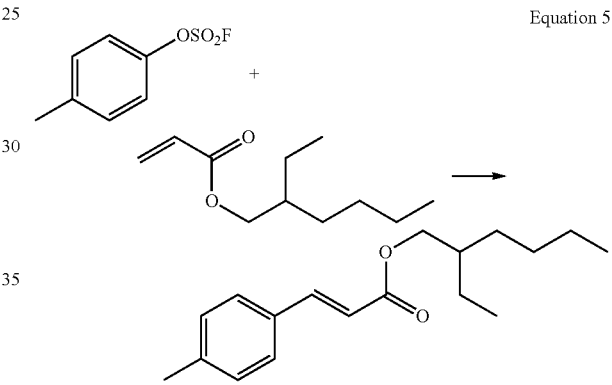

Equation 5

In a $N_2$ filled glovebox, 20 4 mL scintillation vials are each charged with the reactants listed in Table 1. To the reactants is added a palladium precatalyst (palladium acetate (referred to herein as $Pd(OAc)_2$), 5 mol %, 4.5 mg), a ligand (listed in Table 2), a base (listed in Table 3) and a solvent (listed in Table 4). Table 5 lists the Palladium precatalyst, ligand, base and solvent which are added to each vial.

TABLE 1

| Reactant | Equivalents | Amount |
|---|---|---|
| p-tolyl sulfofluoridate | 1 | 0.058 mL |
| 2-ethylhexyl acrylate | 2 | 0.179 g |

TABLE 2

| Ligand | Equivalents | Amount |
|---|---|---|
| Triphenylphosphine (referred to herein as PPh₃) | 0.1 | 0.010 g |
| 1,3-bis(diphenylphosphino)propane (referred to herein as DPPP) | 0.1 | 0.016 g |
| 1,1'-bis(diphenylphosphino)ferrocene (referred to herein as DPPF) | 0.1 | 0.022 g |
| 1,3-bis(diphenylphosphino)ethane (referred to herein as DPPE) | 0.1 | 0.016 g |
| 1,3-bis(diphenylphosphino)propane (referred to herein as DPPB) | 0.1 | 0.017 g |

TABLE 3

| Base | Equivalents | Amount |
|---|---|---|
| Sodium bicarbonate (referred to herein as NaHCO3) | 3 | 0.101 g |
| potassium phosphate (referred to herein as $K_3PO_4$) | 3 | 0.254 g |
| triethylamine (referred to herein as $NEt_3$) | 3 | 0.167 mL |

TABLE 4

| Solvent | Equivalents | Amount |
|---|---|---|
| Dimethylformamide (referred to herein as DMF) | — | 1.2 mL |
| 1,4-dioxane | — | 1.2 mL |
| 1-Butanol | — | 1.2 mL |
| N-methyl-2-pyrrolidone (referred to herein as NMP) | — | 1.2 mL |

TABLE 5

| Vial | Pd Source | Ligand | Base | Solvent | Yield, % |
|---|---|---|---|---|---|
| 1 | Pd(OAc)$_2$ | dppf | Et3N | DMF | 18 |
| 2 | Pd(OAc)$_2$ | dppp | Et3N | DMF | 27 |
| 3 | Pd(OAc)$_2$ | dppb | Et3N | DMF | 18 |
| 4 | Pd(OAc)$_2$ | dppe | Et3N | DMF | 1 |
| 5 | Pd(OAc)$_2$ | PPh3 | Et3N | DMF | 6 |
| 6 | Pd(OAc)$_2$ | dppf | NaHCO3 | DMF | 67 |
| 7 | Pd(OAc)$_2$ | dppp | NaHCO3 | DMF | 81 |
| 8 | Pd(OAc)$_2$ | dppb | NaHCO3 | DMF | 80 |
| 9 | Pd(OAc)$_2$ | dppe | NaHCO3 | DMF | 59 |
| 10 | Pd(OAc)$_2$ | PPh3 | NaHCO3 | DMF | 41 |
| 11 | Pd(OAc)$_2$ | dppf | K3PO4 | DMF | 50 |
| 12 | Pd(OAc)$_2$ | dppp | K3PO4 | DMF | 36 |
| 13 | Pd(OAc)$_2$ |  | K3PO4 | DMF | 0 |
| 14 | Pd(OAc)$_2$ | dppb | K3PO4 | DMF | 24 |
| 15 | Pd(OAc)$_2$ | dppe | K3PO4 | DMF | 38 |
| 16 | Pd(OAc)$_2$ | PPh3 | K3PO4 | DMF | 10 |
| 17 | Pd(OAc)$_2$ | dppp | Et3N | 1,4-dioxane | 24 |
| 18 | Pd(OAc)$_2$ | dppp | NaHCO3 | 1,4-dioxane | 77 |
| 19 | Pd(OAc)$_2$ | dppp | K3PO4 | 1,4-dioxane | 33 |
| 20 | Pd(OAc)$_2$ | PPh3 | K3PO4 | 1,4-dioxane | 12 |

The reaction mixture in each vial is heated to 100° C. for 15 hours with vigorous stirring. Following heating, the reaction mixture in each vial is cooled to room temperature, and thereafter 1 mL of trimethoxybenzene in ethyl acetate (1.33 M solution) is added to the reaction mixture in each vial and each vial is shaken. An aliquot from the organic layer of the reaction mixture of each vial is analyzed by gas chromatography, and the yield of 2-ethylhexyl (E)-3-(p-tolyl)acrylate is determined from the integration of the 2-ethylhexyl (E)-3-(p-tolyl)acrylate peak compared to that of the integration of the trimethoxybenzene peak. The yield of 2-ethylhexyl (E)-3-(p-tolyl)acrylate for each vial is listed in Table 5.

Example 2

Substituted Penyl or Heteroaryl Sulfofluoridate and 2-Ethylhexyl Acrylate Reacted to Yield 2-Ethylhexyl (E)-3-(Substituted Phenyl or Heteroaryl)Acrylate In this Example, substituted penyl or heteroaryl sulfofluoridate and 2-ethylhexyl acrylate are reacted to yield 2-ethylhexyl (E)-3-(substituted phenyl or heteroaryl)acrylate in Equation 3, -FG is a generic identifier that designates a functional group which is bonded to the ring at a desired position.

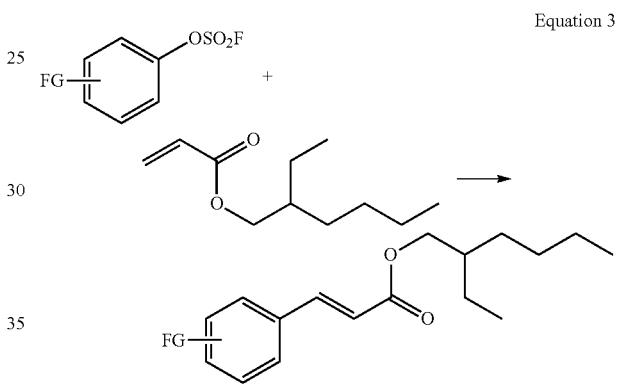

Equation 3

In a N$_2$ filled glovebox, ten 4 mL scintillation vials are charged with (1 mmol, 1 equivalent) of the functionalized fluorosulfonate identified in Table 6. (2 mmol, 2 equivalents) of 2-ethylhexyl acrylate are added to each vial. To each vial is added Pd(OAc)2 precatalyst (4.5 mg, 2 mol %), dppp (12.4 mg, 3 mol %), Na2HCO3 (0.168 g, 2.0 mmol, 2 equivalents) and DMF to have 2 mL altogether volume. The reaction mixture is stirred for 15 hours at 100° C. The reaction mixture is impregnated on silica gel and the product identified in Table 6 is the isolated yield is calculated using column chromatography and recorded in Table 6.

TABLE 6

| Vial | Fluorosulfonate | Product | Yield, mg | Isolated yield, % |
|---|---|---|---|---|
| 1 | 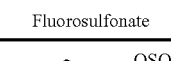 | 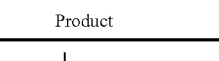 | 222 | 81 |

TABLE 6-continued

| Vial | Fluorosulfonate | Product | Yield, mg | Isolated yield, % |
|---|---|---|---|---|
| 2 | 2,4-dimethylphenyl fluorosulfonate | 2-ethylhexyl (E)-3-(2,4-dimethylphenyl)acrylate | 184 | 64 |
| 3 | 3-(phenylcarbamoyl)phenyl fluorosulfonate | 2-ethylhexyl (E)-3-(3-(phenylcarbamoyl)phenyl)acrylate | 265 | 70 |
| 4 | 6-methylpyridin-3-yl fluorosulfonate | 2-ethylhexyl (E)-3-(6-methylpyridin-3-yl)acrylate | 168 | 61 |
| 5 | benzo[d][1,3]dioxol-5-yl fluorosulfonate | 2-ethylhexyl (E)-3-(benzo[d][1,3]dioxol-5-yl)acrylate | 268 | 88 |
| 6 | 4-methoxyphenyl fluorosulfonate | 2-ethylhexyl (E)-3-(4-methoxyphenyl)acrylate | 223 | 77 |

TABLE 6-continued

| Vial | Fluorosulfonate | Product | Yield, mg | Isolated yield, % |
|---|---|---|---|---|
| 7 | | | 282 | 85 |
| 8 | | | 262 | 80 |
| 9 | | | 191 | 65 |
| 10 | | | 218 | 69 |

Example 3

In this Example, 4-Methoxyphenyl-sulfofluoridate is reacted with styrene as shown in Equation.

Equation 4

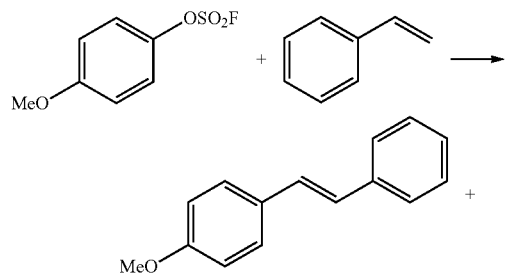

-continued

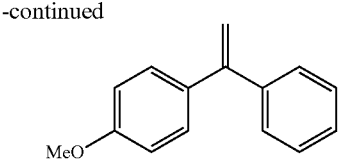

A 3-neck 50 mL round bottom flask equipped with a condenser, magnetic stir bar and nitrogen inlet is provided as a reaction vessel. 1.00 grams of 4-Methoxyphenyl-sulfofluoridate is added to the reaction vessel followed by 2.78 mL of styrene. 15.16 mL dimethylformamide (referred to herein as DMF) is added by syringe to the reaction vessel followed by 0.222 g Tris(dibenzylideneacetone)dipalladium (0) (referred to herein as $Pd_2(dba)_3$) and 0.200 g 1,3-bis (diphenylphosphino)propane (referred to herein as DPPP). The contents of the reaction vessel are stirred after which 0.81 mL triethylamine (referred to herein as NEt$_3$) is added. The contents of the reaction vessel are then heated to 80° C. with constant stirring. Following 40 minutes of stirring at 80° C., a sample of the contents of the reaction vessel is analyzed with gas chromatograph analysis and is found to have 99% conversion of the 4-Methoxyphenyl-sulfofluoridate. The contents of the reaction vessel are then allowed to stir at 80° C. overnight, following which a sample of the reaction vessel is analyzed with gas chromatograph analysis and is found to have complete conversion of the 4-Methoxyphenyl-sulfofluoridate. A sample of the contents of the reaction vessel is analyzed by gas chromatograph analysis and is found to contain two isomers of the product present in approximately a 1 to 1 ratio, as represented in Formula 1 and Formula 2. The contents of the reaction vessel is purified by flash chromatography using a CombiFlash purification system to provide 310 mg of compound with Formula 1 as a white solid and 220 mg of compound with Formula 2 as a white solid. The combined isolated yield for the reaction is 56%. NMR analysis on the product corresponding to Formula 1: $^1$H NMR (400 MHz, Chloroform-d) δ 7.44-7.32 (m, 4H), 7.30-7.20 (m, 2H), 7.19-7.10 (m, 1H), 6.98 (d, J=16.3 Hz, 1H), 6.88 (d, J=16.3 Hz, 1H), 6.83-6.79 (m, 2H), 3.73 (s, 3H). NMR analysis on the product corresponding to Formula 2: $^1$H NMR (400 MHz, Chloroform-d) δ 7.27-7.20 (m, 5H), 7.20-7.16 (m, 2H), 6.79-6.74 (m, 2H), 5.30 (d, J=1.3 Hz, 1H), 5.26 (d, J=1.3 Hz, 1H), 3.71 (s, 3H).

Formula 1

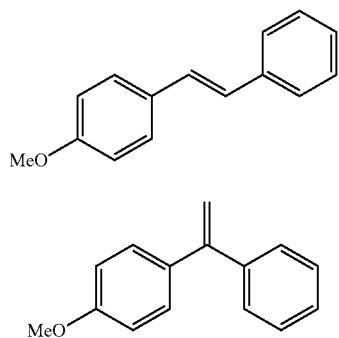

Formula 2

Example 4

In this Example, p-tolyl sulfofluoridate is reacted with styrene as shown in Equation 6.

Equation 6

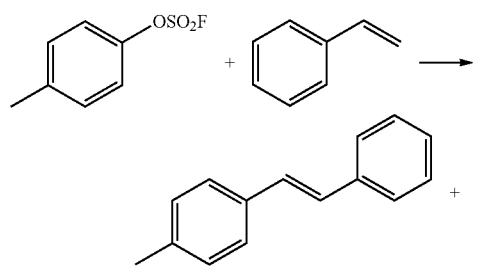

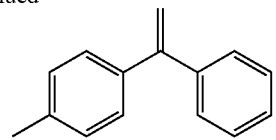

A 3-neck 50 mL round bottom flask equipped with a condenser, magnetic stir bar and nitrogen inlet is provided as a reaction vessel. 0.50 grams of p-tolyl sulfofluoridate is added to the reaction vessel followed by 0.60 mL of styrene. 8.2 mL DMF is added by syringe to the reaction vessel followed by 0.120 g Pd$_2$(dba)$_3$ and 0.108 g DPPP. The contents of the reaction vessel are stirred after which 0.44 mL NEt$_3$ is added. The contents of the reaction vessel are then heated to 80° C. with constant stirring. Following 5.5 hours of stirring at 80° C. a sample of the contents is analyzed with gas chromatograph analysis and is found to have 70% conversion of the p-tolyl sulfofluoridate. The contents of the reaction vessel are then allowed to stir at 80° C. overnight, following which a sample of the reaction vessel is analyzed with gas chromatograph analysis and is found to have complete conversion of the p-tolyl sulfofluoridate. A sample of the contents of the reaction vessel is analyzed by gas chromatograph analysis and is found to contain two isomers of the product present in approximately a 1.4 to 1 ratio, as represented in Formula 3 and Formula 4. The contents of the reaction vessel is purified by flash chromatography using a CombiFlash purification system to provide 207 mg of compound with Formula 3 as a white solid and 164 mg of compound with Formula 4 as a white solid. The combined isolated yield for the reaction is 72.8%. NMR analysis on the product corresponding to Formula 3: $^1$H NMR (400 MHz, Chloroform-d) δ 7.42-7.37 (m, 2H), 7.33-7.29 (m, 2H), 7.27-7.21 (m, 2H), 7.17-7.11 (m, 1H), 7.08-7.04 (m, 2H), 6.98 (s, 1H), 6.97 (s, 1H), 2.25 (s, 3H). NMR analysis on the product corresponding to Formula 4: $^1$H NMR (400 MHz, Chloroform-d) δ 7.27-7.19 (m, 5H), 7.16-7.12 (m, 2H), 7.06-7.01 (m, 2H), 5.33 (d, J=1.3 Hz, 1H), 5.31 (d, J=1.3 Hz, 1H), 2.26 (s, 3H).

Formula 3

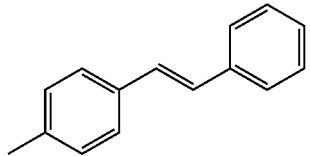

Formula 4

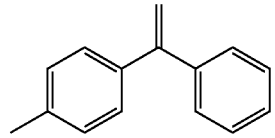

Example 5

In this Example, 4-Methoxyphenyl-sulfofluoridate is reacted with 1-octene as shown in Equation 7.

Equation 7

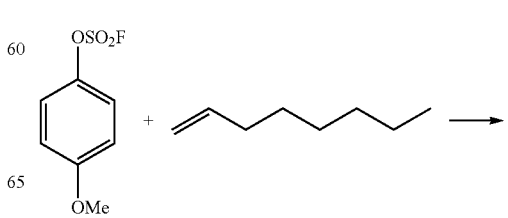

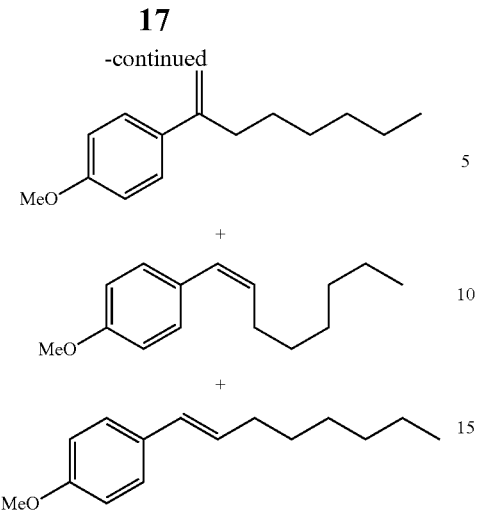

A 3-neck 50 mL round bottom flask equipped with a condenser, magnetic stir bar and nitrogen inlet is provided as a reaction vessel. 1.00 grams of 4-Methoxyphenyl-sulfofluoridate is added to the reaction vessel followed by 1.52 mL of 1-octene. 15.16 mL DMF is added by syringe to the reaction vessel followed by 0.388 g $Pd_2(dba)_3$ and 0.320 g DPPP. The contents of the reaction vessel are stirred after which 0.81 mL $NEt_3$ is added. The contents of the reaction vessel are then heated to 80° C. with constant stirring. Following 3.5 hours of stirring at 80° C. a sample of the contents of the reaction vessel is analyzed with gas chromatograph analysis and is found to have 93.5% conversion of the 4-Methoxyphenyl-sulfofluoridate. The contents of the reaction vessel are then allowed to stir at 80° C. for another hour, following which a sample of the reaction vessel is analyzed with gas chromatograph analysis and is found to have 97.6% conversion of the 4-Methoxyphenyl-sulfofluoridate. A sample of the contents of the reaction vessel is analyzed by gas chromatograph analysis and is found to contain three isomers of the product. Crude NMR yields a 7:5:1 ratio, as represented in Formula 5, Formula 6 and Formula 7. The combined isolated yield for the reaction is 83.9%. The contents of the reaction vessel are purified by flash chromatography using a CombiFlash purification system to afford 211 mg of compound with Formula 5 as a white solid and 678 mg of a mixture of compounds with Formula 5, 6 and 7. After isolation of Formula 5, the NMR for the combined mixtures of Formula 5, 6 and 7 are in a ratio of 2:2:1 based on the integration of peaks at 6.14 ppm, 5.77 ppm and 5.25 ppm. NMR analysis on the product corresponding to Formula 5: $^1$H NMR (400 MHz, Chloroform-d) δ 7.33-7.22 (m, 2H), 6.82-6.70 (m, 2H), 5.10 (d, J=1.6 Hz, 1H), 4.88 (q, J=1.4 Hz, 1H), 3.71 (s, 3H), 2.42-2.33 (m, 2H), 1.60-1.11 (m, 8H), 0.79 (t, J=6.6 Hz, 3H).

Formula 5

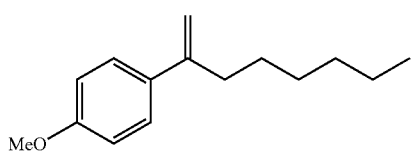

Formula 6

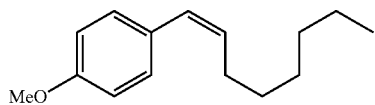

Formula 7

Example 6

In this Example, 2-ethylhexyl (E)-3-(p-tolyl)acrylate is prepared in a one-pot reaction as illustrated in Equation 8.

Equation 8

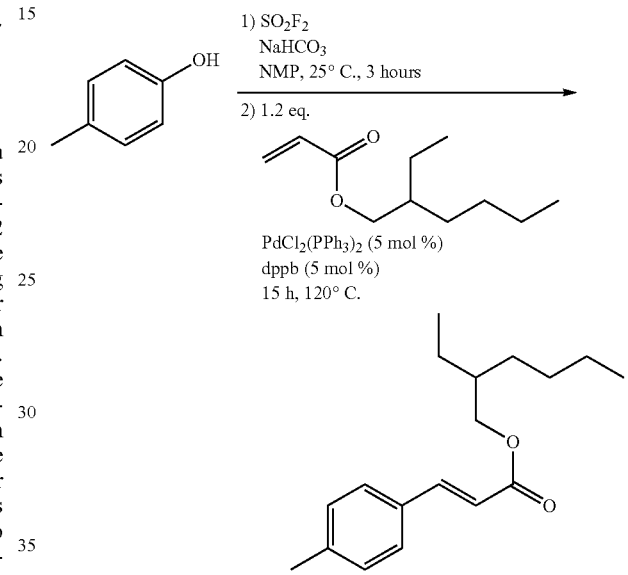

To a 30 mL vial is added p-cresol derivative (216 mg, 2.0 mmol) and $NaHCO_3$ (504 mg, 6.0 mmol). To the mixture is added 15 mL of dry NMP. The vial is tightly capped and to the stirring reaction mixture is added $SO_2F_2$ by slow bubbling via needle at room temperature for 3 h. The reaction mixture is next purged with $N_2$ for 30 mins. The vial is then transferred to an $N_2$-filled glovebox, and in the following order, 2-ethylhexyl acrylate (442 mg, 2.4 mmol), PdCl2(PPh3)2 (70 mg; 0.1 mmol) and diphenylphosphinobtane (dppb, 42 mg; 0.1 mmol) are added to the vial. The reaction mixture is stirred for 15 h at 120° C. The reaction mixture is next cooled to room temperature and adsorbed onto silica gel. The product is then purified by flash chromatography (ISCO) and the volatiles are removed by vacuum to reveal the desired product. Purification by flash chromatography (hexane:ethyl acetate gradient) revealed 1-([1,1'-biphenyl]-4-yl)ethanone as a white solid (450 mg, yield 82%).

What is claimed is:
1. A method of coupling a first compound $A^1$ to a second compound $A^2$, the method comprising:
providing the first compound $A^1$ comprising an aryl group having a fluorosulfonate substituent of the formula —$OSO_2F$ or heteroaryl group having a fluorosulfonate substituent of the formula —$OSO_2F$;
providing the second compound $A^2$:

$A^2$ $$\underset{R}{\overset{R}{HC}}=\underset{R}{\overset{R}{C}}$$

wherein each R substituent is independently Hydrogen, an aryl group, a heteroaryl group, an alkyl group, a cycloalkyl group, a nitro group, a halide, a nitrogen, a cyano group, a carboxyester group, an acetoxy group, a substituted alkyl, aryl, heteroaryl or cycloalkyl group, or any two of the R groups are constituent parts of a ring system; and reacting the first compound $A^1$ and the second compound $A^2$ in a reaction mixture, the reaction mixture including a catalyst having at least one group 10 atom, the reaction mixture under conditions effective to couple the first compound $A^1$ to the second compound $A^2$.

2. The method of claim 1, wherein the reaction mixture further includes a ligand.

3. The method of claim 1 wherein the catalyst is generated in-situ from a palladium precatalyst.

4. The method of claim 1 wherein the catalyst is generated in-situ from a palladium precatalyst, the palladium precatalyst is selected from the group consisting of: Palladium(II) acetate, Palladium(II) chloride, Dichlorobis(acetonitrile)palladium(II), Dichlorobis(benzonitrile)palladium(II), Allylpalladium chloride dimer, Palladium(II) acetyl acetonate, Palladium(II) bromideBis(dibenzylideneacetone)palladium(0), Bis(2-methylallyl)palladium chloride dimer, Crotylpalladium chloride dimer, Dichloro(1,5-cyclooctadiene)palladium(II), Dichloro(norbornadiene)palladium(II), Palladium(II) trifluoroacetate, Palladium(II) benzoate, Palladium(II) trimethylacetate, Palladium(II) oxide, Palladium(II) cyanide, Tris(dibenzylideneacetone)dipalladium(0), Palladium(II) hexafluoroacetylacetonate, cis-Dichloro(N,N,N',N'-tetramethylethylenediamine)palladium(II), and Cyclopentadienyl[(1,2,3-n)-1-phenyl-2-propenyl]palladium(II), [1,3-Bis(2,6-Diisopropylphenyl)imidazol-2-ylidene](3-chloropyridyl)palladium(II) dichloride, and (1,3-Bis(2,6-diisopropylphenyl)imidazolidene) (3-chloropyridyl) palladium(II) dichloride, and a mixture of two or more thereof.

5. The method of claim 2 wherein the ligand is a phosphine ligand or a carbene ligand.

6. The method of claim 2 wherein the ligand is an amine-based ligand, an aminophosphine-based ligand, an N-heterocyclic carbene-based ligand, a monodentate or bidentate alkyl amine, or a monodentate or bidentate aromatic amine.

7. The method of claim 1 wherein the reaction mixture includes a base.

8. The method of claim 7, wherein the base is a carbonate salt, a phosphate salt, an acetate salt or a carboxylic acid salt.

9. The method of claim 7, wherein the base is selected from the group consisting of lithium carbonate, sodium carbonate, potassium carbonate, rubidium carbonate, cesium carbonate, ammonium carbonate, substituted ammonium carbonates, hydrogen carbonates, lithium phosphate, sodium phosphate, potassium phosphate, rubidium phosphate, cesium phosphate, ammonium phosphate, substituted ammonium phosphates, hydrogen phosphates, lithium acetate, sodium acetate, potassium acetate, rubidium acetate, cesium acetate, ammonium acetate, substituted ammonium acetates, formate salts, fluoroacetate salts, propionate anions with lithium, sodium, potassium, rubidium, cesium, ammonium, and substituted ammonium cations, lithium hydroxide, sodium hydroxide, potassium hydroxide, magnesium dihydroxide, calcium dihydroxide, strontium dihydroxide, and barium dihydroxide, aluminum trihydroxide, gallium trihydroxide, indium trihydroxide, thallium trihydroxide, triethylamine, N,N-diisopropylethylamine, 1,4-diazabicyclo[2.2.2]octane, 1,5-Diazabicyclo[4.3.0]non-5-ene, 1,8-Diazabicyclo[5.4.0]undec-7-ene, lithium, sodium, and potassium salts of bis(trimethylsilyl)amide, lithium, sodium, and potassium salts oft butoxide, 1,8-bi s(dimethylamino)naphthalene, pyridine, morpholine, 2,6-lutidine, triethylamine., N,N-Dicyclohexylmethylamine, diisopropylamine, sodium fluoride, potassium fluoride, cesium fluoride, silver fluoride, tetra butyl ammonium fluoride, ammonium fluoride, triethyl ammonium fluoride and a mixture of two or more thereof.

10. The method of claim 1, wherein the reaction mixture includes a solvent.

11. The method of claim 10, wherein the solvent is selected from the group consisting of toluene, xylene, benzene, chlorobenzene, water, methanol, ethanol, 1-propanol, 2-propanol, n-butanol, 2-butanol, pentanol, hexanol, tent-butyl alcohol, tent-amyl alcohol, ethylene glycol, 1,2- propanediol, 1,3-propanediol, glycerol, N-methyl-2-pyrrolidone, acetonitrile, N,N-dimethylformamide, methyl acetate, ethyl acetate, propyl acetate, isopropyl acetate, triacetin, acetone, methyl ethyl ketone, ethereal solvents, 1,4-dioxane, tetrahydrofuran, 2-methyltetrahydrofuran, diethylether, cyclopenyl methyl ether, 2-butyl ethyl ether, dimethoxyethane, polyethyleneglycol, dimethylacetamide(DMA), dimethylsulfoxide (DMSO), and 1,2-dichloroethane (DCE).

12. The method of claim 1, wherein the reaction mixture includes water.

13. A method for coupling a first compound $A^1$ to a second compound $A^2$, as illustrated in Equation 1, comprising:

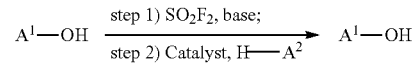

Equation 1 providing sulfuryl fluoride, a base and the first compound $A^1$ comprising an aryl having a hydroxyl substituent or a heteroaryl group having a hydroxyl substituent to a reaction mixture, the first compound comprising an aryl or a heteroaryl group;

providing a catalyst having at least one group 10 atom and the second compound $A^2$ to the reaction mixture:

wherein each R substituent is independently Hydrogen, an aryl group, a heteroaryl group, an alkyl group, a cycloalkyl group, a nitro group, a halide, a nitrogen, a cyano group, a carboxyester group, an acetoxy group, a substituted alkyl, aryl, heteroaryl or cycloalkyl group, or any two of the R groups are constituent parts of a ring system; and allowing the reaction mixture to react under conditions to produce the product shown in Equation 1.

14. The method of claim 13, wherein the reaction mixture further includes a ligand, and a base.

15. The method of claim 13 wherein the catalyst is generated in-situ from a palladium precatalyst.

16. The method of claim 14 wherein the ligand is a phosphine ligand or a carbene ligand.

17. The method of claim 14 wherein the ligand is an amine-based ligand, an aminophosphine-based ligand or an N-heterocyclic carbene-based ligand.

18. The method of claim 14 wherein the ligand is a monodentate or bidentate alkyl amine or a monodentate or bidentate aromatic amine.

19. The method of claim 14, wherein the base is a carbonate salt, a phosphate salt, an acetate salt or a carboxylic acid salt.

20. The method of claim 13, wherein the reaction mixture includes a solvent.

\* \* \* \* \*